US009376674B2

(12) United States Patent
Jorquera Nieto et al.

(10) Patent No.: US 9,376,674 B2
(45) Date of Patent: Jun. 28, 2016

(54) PROCESS TO PREPARE A STABLE THROMBIN COMPOSITION

(71) Applicant: GRIFOLS, S.A., Barcelona (ES)

(72) Inventors: Juan Ignacio Jorquera Nieto, Barcelona (ES); Pere Ristol Debart, Sabadell (ES); Jesus Fernandez Rodriguez, Gava (ES); Isabel Bravo Camison, Manresa (ES); Rafael Lopez Gomez, Vigo (ES)

(73) Assignee: GRIFOLS, S.A., Barcelona (ES)

( * ) Notice: Subject to any disclaimer, the term of this patent is extended or adjusted under 35 U.S.C. 154(b) by 0 days.

(21) Appl. No.: 14/327,686

(22) Filed: Jul. 10, 2014

(65) Prior Publication Data
US 2014/0322791 A1 Oct. 30, 2014

Related U.S. Application Data

(62) Division of application No. 11/251,566, filed on Oct. 13, 2005, now abandoned.

(30) Foreign Application Priority Data

Oct. 22, 2004 (ES) .................... 200402523

(51) Int. Cl.
| | | |
|---|---|---|
| *C12N 9/74* | (2006.01) | |
| *C12N 9/96* | (2006.01) | |
| *A61K 9/19* | (2006.01) | |
| *A61K 38/48* | (2006.01) | |
| *A61K 47/02* | (2006.01) | |
| *A61K 47/42* | (2006.01) | |

(52) U.S. Cl.
CPC ... *C12N 9/96* (2013.01); *A61K 9/19* (2013.01); *A61K 38/4833* (2013.01); *C12N 9/6429* (2013.01); *A61K 47/02* (2013.01); *A61K 47/42* (2013.01)

(58) Field of Classification Search
None
See application file for complete search history.

(56) References Cited

U.S. PATENT DOCUMENTS

| | | | |
|---|---|---|---|
| 4,696,812 A | 9/1987 | Silbering et al. | |
| 4,923,815 A | 5/1990 | Tanaka et al. | |
| 5,149,540 A | 9/1992 | Kunihiro et al. | |
| 5,304,372 A * | 4/1994 | Michalski et al. | 424/94.64 |
| 5,476,777 A | 12/1995 | Holly et al. | |
| 5,506,127 A * | 4/1996 | Proba et al. | 435/214 |
| 5,907,032 A * | 5/1999 | MacGregor et al. | 530/384 |
| 5,981,254 A * | 11/1999 | Bui-Khac | 435/214 |
| 2001/0051154 A1 | 12/2001 | Roemisch et al. | |

FOREIGN PATENT DOCUMENTS

| | | |
|---|---|---|
| EP | 0444692 | 9/1991 |
| EP | 1221479 | 7/2002 |
| ES | 2108738 T3 | 1/1998 |
| JP | 56 039782 | 4/1981 |
| JP | 10215875 | 8/1998 |
| WO | WO 96/09376 | 3/1996 |
| WO | WO 99/23111 | 5/1999 |

OTHER PUBLICATIONS

Burnouff et al. Haemophilia, 2003, vol. 9, pp. 24-37.*
Anonymous: "Thrombostat" Internet Article 'Online, Oct. 28, 2001, XP002369173, Retrieved from the Internet: URL:https://www.eknowhow.com/ekh_drugdatabse/html/default.asp?> retireved on Feb. 21, 2006, p. 1, paragraph 1.
Burnouf et al., "Nanofiltratin of plasma-derived biopharmaceutical products". Haemophilia 9:24-37 (2003).

* cited by examiner

*Primary Examiner* — Vera Afremova
(74) *Attorney, Agent, or Firm* — Leason Ellis LLP

(57) ABSTRACT

The stable thrombin composition comprises purified thrombin, human albumin and a neutral salt, the resulting product being stable when stored as a lyophilisate or frozen and is adjusted to a nominal strength of 500 IU of thrombin or more per ml of solution, the human albumin being in a concentration of over 0.05% (w/v) and preferably between 0.1% (w/v) and 1% (w/v).

8 Claims, No Drawings

PROCESS TO PREPARE A STABLE THROMBIN COMPOSITION

CROSS-REFERNCE TO RELATED APPLICATIONS

This present application is a Divisional of U.S. patent application Ser. No. 11/251,566, filed Oct. 13, 2005, which claims priority to Spanish Patent Application No. 200402523, filed Oct. 22, 2004, each of which is incorporated herein by reference in its entirety.

This invention relates to a thrombin composition which is stable in solution for therapeutic use as a component of fibrin adhesives or for other haemostatic uses, which may be subjected to double nanofiltration in order to retain viruses, and which may be preserved in the lyophilised or frozen condition.

PRIOR ART

Thrombin is a serine protease generated in circulating blood through the activation of its inactive precursor, prothrombin. It has a fundamental role in the coagulation process, splitting the fibrinogen molecule into fibrin monomers in order to form the fibrin coagulate, in order to maintain haemostasis. Thus thrombin has therapeutic applications as a local haemostatic agent and as a component of fibrin adhesives (compounds comprising mainly fibrinogen and thrombin as active ingredients).

The thrombin in conventional use has been of animal origin (bovine or equine). These preparations have in many cases given rise to immunological reactions due to a heterologous protein overload. In recent years human thrombin has been purified from human plasma with significant degrees of purification, and more recently it has been possible to obtain human thrombin of recombinant origin on an industrial scale having an activity identical to that of thrombin of plasma origin [Biochem. (Tokyo) 2004 May; 135(5):577-582] or of transgenic origin.

Purified thrombin solutions of whatever origin give rise to stability problems both during the final stages of the production process and during storage for marketing (stability of the final product), and may suffer a significant loss of activity if not adequately stabilised.

In addition to this, as a product of biological origin, thrombin must be subjected to specific stages to eliminate pathogenic agents associated with the starting material where it has its origin in plasma, or associated with the culture media in the case of recombinant products or the producing organisms in the case of transgenic products. The current trend is to include at least two supplementary virus elimination stages.

Because of their wide use and marked efficiency, among the methods used for reducing the viral load in the processes for purifying plasma proteins mention should be made, of:

Thermal treatments. These potentially reduce the effective viral load of both enveloped and naked viruses. Its efficiency is directly related to the thermal stability of the protein and the added stabiliser, it being necessary to avoid further changes in the protein molecule which induce the occurrence of neoantigenicity [CPMP/Note for guidance on plasma derived products (CPMP/BWP/269/95rev. 3) January 2001].

Organic solvent (OSD) treatments. Because of their great efficiency in inactivating viruses with a lipid envelope these are a widely used form of treatment which can be regarded as the reference treatment for this type of viruses. Conversely they have no effect on viruses without a lipid envelope, such as Parvovirus and Hepatitis A virus [Burnouf T. Blood Reviews (2000) 14, 94-110; Martinowitz U. Curr. Opin. Hematol. (1996) 3, 395-402].

The filtration of solutions through filters of a pore size capable of holding back viral particles is one method which has become widely used in recent years because it is a physical process which in principle has no potential capability to change the structure of the proteins and has an effective ability in eliminating viral load, depending upon the pore size used. This pore size is especially chosen for the spatial dimensions of the protein molecule which has to be filtered (which must pass through the filter). Filtration through 15 nm filters can guarantee a significant reduction in small naked viruses such as Hepatitis A virus and Parvovirus, which lie between 20 and 30 nm. The possibility of carrying out filtration in series using two 15 nm filters would increase the level of reduction in viral load and thus the level of safety with regard to these viruses. If this nanofiltration is carried out in a final stage, which avoids subsequent concentration operations and adjustment in the composition of the solution, it cancels out the possibility of accidental contamination of the nanofilter product.

The following documents may also be cited:

Patent ES 2108738 (Michalski), which describes a process for the preparation of thrombin, establishes a formulation combining gluconate buffer with 2 g/l of albumin, 5 g/l of saccharose and 60 mM of $CaCl_2$, indicating that the albumin, saccharose and calcium are essential for stabilisation during handling in solution (24 hours stability), freezing and subsequent lyophilisation.

Application PCT WO 99/23111 (Haemacure), which describes a process for obtaining fibrinogen and thrombin as components of a fibrin adhesive, specifies that in order to preserve thrombin activity it is essential that albumin be added immediately after elution. The concentration of albumin added for stabilisation and formulation is 2%.

DESCRIPTION OF THE INVENTION

The inventors have developed a thrombin formulation which is highly purified in the presence of human albumin and a neutral salt and possibly a solubilising agent and pH buffer.

This formulation is nanofilterable, in series, through two filters of nominal pore size of up to 35 nm, and preferably 15 nanometers (nm), having a high filtration capacity and without any fall in product recovery or deterioration of the nanofiltered material, such that even the smallest viruses such as monodispersed porcine parvovirus (as a model of human B19) are retained to a level of more than log 4 (base 10). Likewise the nanofiltered material does not require subsequent treatment for adjustment of the formula or final composition, avoiding any risk of cross-contamination, the product obtained being sufficiently stable for subsequent processing, and is stored stably in a lyophilised or frozen state.

In this formulation the albumin acts as a stabiliser and preserves the activity of the thrombin during manipulation in the liquid state, in the process of nanofiltration, and during lyophilisation or freezing. Likewise the albumin has an effect as a pH buffer and imparts compactness to the lyophilised pellet. As far as the neutral salt, such as sodium chloride, is concerned, this acts to dissolve the thrombin and maintain the isotonicity of the solution, given that thrombin is very insoluble and precipitates out at a low ionic strength.

The pH damping effect and also the compacting and solubilisation of the lyophilisate can be complemented through the addition of a solubilising agent and/or pH buffer such as glycine, or sodium citrate or acetate.

The inventors have established that albumin concentrations in excess of 0.05% and the presence of sodium chloride are necessary. The sodium chloride concentration must be at least 0.05 molar, and better still if it is approximately isotonic or 0.15 molar. In this way the thrombin solution can be doubly nanofiltered through filters of nominal pore size of up to 35 nm, and preferably 15 nm, with good productivity (up to 15 million IU of thrombin per $m^2$ of nanofiltration area, or even higher loading) without observing any significant loss of activity (thrombin recovery>90%). The nanofiltered material is sterilised using a 0.2 µm membrane and is aseptically metered into an appropriate container (vial, bottle, syringe, etc.) and frozen at $-18°$ C. for subsequent lyophilisation, or stored in the frozen state. In the latter case it is possible to adjust the formula through adding calcium chloride solution to the thrombin before freezing, without this affecting its stability.

A process for obtaining a composition according to the invention is described below, by way of an example which is explanatory but non-restrictive:

The thrombin solution purified by a method which gives rise to a product having specific activity characteristics equal to 1500 IU of thrombin/mg of protein or more and a potential of 500 IU of thrombin/ml or more is stabilised by adding and mixing with human albumin at a concentration of over 0.05% (w/v), and preferably between 0.1% and 1% (w/v) and sodium chloride at a concentration of 0.05 molar or higher and at a pH of between 5.0 and 8.5.

This thrombin solution is treated using a double nanofiltration system up to a nominal pore size of up to 35 nm, and preferably 15 nm. The type of nanofilter used is marketed under the name Planova 15N® (from Asahi-Kasei) and has the configuration of a hollow fibre cartridge of regenerated cellulose with different filtration areas. Under the specific conditions of formulation it is possible to perform the double nanofiltration simultaneously through connecting the two nanofilters in series in such a way that the filtrate from the first feeds the second and without thereby changing the nanofiltration conditions recommended by the manufacturer of these nanofilters, corresponding to a positive differential pressure of less than 1.0 bar and preferably between 0.2 bar and 1.0 bar in each nanofilter. The nanofiltration capacity per filter may be greater than 30 $l/m^2$, although in order to achieve efficient reduction of the smallest viruses (parvovirus) preferably not more than 30 litres of solution are applied per $m^2$, more preferably between 5 and 30 $l/m^2$.

The nanofiltered liquid may have a nominal strength of approximately 500 IU/ml without additional handling given that it is already adjusted to the final formula, for either lyophilisation or subsequent freezing.

In order to adjust the final formula it is possible when required, for example, to add amino acids such as glycine in a concentration of between 0.01 and 0.1 Molar, salts of carboxylic acids, such as sodium citrate or acetate at a concentration of, for example, 10 mM and calcium chloride or equivalent salts (normally between 20 and 60 mM). The resulting formulation continues to be nanofilterable and stable during this process.

The product obtained is stable for a long period of time, both when lyophilised and when frozen. The lyophilised product may also be optionally subjected to viral inactivation through heat at high temperature with a short exposure time, for example between 90 and 115° C. for 0.5-8 hours, and preferably 1-2 hours at approximately 100° C.

The characteristics of the invention can be summarised as:

A purified thrombin composition whose formula comprises human albumin and a neutral salt such as sodium chloride, the resulting product being stable when stored either frozen or lyophilised. In this composition the thrombin is adjusted to a nominal strength of 500 IU of thrombin per ml of solution or more, and the human albumin is adjusted to a concentration of over 0.05% (w/v) and preferably between 0.1% and 1% (w/v). The sodium chloride concentration should be at least 0.05 molar, and better still if approximately isotonic or 0.15 molar.

This thrombin composition can be filtered by double nanofiltration in series up to a nominal pore size of up to 35 nm and preferably 15 nm, it being possible to filter up to 30 litres of solution per $m^2$ of filtration area in each nanofilter.

This lyophilised thrombin composition may be treated by dry heat for between a ½ hour and 8 hours at 90-115° C., and preferably for 1-2 hours at 100° C.

Various non-restrictive examples of the invention are described below.

EXAMPLE 1

A purified thrombin (lot T-1006) having a specific activity >1500 IU/mg of total protein was dialysed using 10 kDa ultrafiltration membranes against 5 volumes of a solution containing 75 mM of NaCl, 50 mM of glycine and 10 mM of sodium acetate at pH 6.5, finally being concentrated to 654 IU of thrombin/ml of solution. This was subsequently stabilised through the addition of up to 0.25% of human albumin (Albúmina Grifols 20%)

The solution stabilised in this way was frozen at <$-20°$ C. to begin the nanofiltration tests. The effect of prior prefiltration (clarification) on double nanofiltration up to a 15 nm nominal pore size was investigated using regenerated cuprammonium cellulose nanofilters (Planova 15N®, from Asahi-Kasei). For this purpose three aliquots of the stabilised solution were thawed in a water bath at 20±2° C. so that the final temperature of the product was between 2 and 8° C., the thrombin activity was between 591.0 and 614.5 IU/ml, and the total protein was between 2.54 and 2.80 mg/ml. The solutions were independently prefiltered using 3 types of filter of different pore size: 0.22 μm (PVDF, from Millipore), 0.1 μm (PVDF, from Pall Corp.) and 35 nm (regenerated cuprammonium cellulose, Planova 35N® from Asahi-Kasai); and subsequently by double 15 nm nanofiltration (2× Planova 15N® from 0.001 m²) simultaneously, performing a final post-wash with the equivalent of 20-28% of the initial volume of product. The viability of the process and the effect of prefiltration was tested with regard to the application ratio obtained (kg/m²), the change or increase in the transmembrane pressure (TMP) during nanofiltration, total protein, thrombin activity and thrombin recovery.

The test conditions and the results obtained were as follows:

| DOUBLE NANOFILTRATION USING 15 nm (2 × PLANOVA 15N) | | | |
| --- | --- | --- | --- |
| Type of prior prefiltration | 35 nm | 0.1 μm | 0.22 μm |
| Application ratio (kg/m²) | 30.01 | 30.15 | 30.02 |
| TMP for the 2$^{nd}$ Planova 15N (bar) | 0.20-0.85 | 0.20-0.95 | 0.20-0.80 |
| Filtration flow (kg/h/m2) | 3.36 | 3.80 | 3.69 |
| Filtration time | 11 h 31 min. | 9 h 10 min. | 9 h 43 min. |
| Filtrate protein (mg/ml) | 2.33 | 2.62 | 2.52 |
| Filtrate activity (UI/ml) | 442.5 | 504.6 | 470.0 |
| Recovery of activity (%) | 99.0 | 99.3 | 96.9 |

From the investigation it will be seen that prefiltering of the formulated material previously frozen at <−20° C. has no differential effect on the double nanofiltration at 15 nm within the pore size range studied from 0.22 μm to 35 nm, as regards increase in TMP during nanofiltration, for approximately the same application ratio and filtrate flow. Also there were no significant differences in relation to protein, activity and % recovery between the tests made. Likewise the viability of double nanofiltration at 15 nm with the product formula developed containing highly purified thrombin and albumin, together with sodium chloride, glycine and sodium acetate, with application ratio values >30 kg/m² and recoveries of over 96% in all cases, has been demonstrated.

EXAMPLE 2

The possibility of subjecting the final product dried by lyophilisation to very high temperature short exposure heat treatment was investigated. Starting from the same lot of purified product the formulation was prepared in two different compositions: Formula A: approximately 500 IU/ml of protein thrombin, 1% albumin, 10 mM sodium acetate and 75 mM sodium chloride; Formula B: approx. 500 IU/mL of thrombin, 2% mannitol, 10 mM histidine, 0.03% of PEG-3350 and 175 mM of sodium chloride.

The compositions were nanofiltered at 15 nm and the nanofiltered product was lyophilised in 10 ml vials, performing a final 24 hour drying at 37° C. under the maximum vacuum conditions of the equipment (<0.1 mbar), leaving a residual moisture content of less than 1%.

The vials obtained were subjected to heat treatment at temperatures of 100° C., 105° C., 110° C. and 115° C., for periods of ½ h, 1 h, 2 h, 4 h and 8 h, with subsequent determination of the thrombin activity. The percentage activity recoveries in relation to the initial product not subjected to heat treatment are shown below:

| Temperature (° C.) | Hours exposure | Recovery of activity (%) Formula A | Formula B |
| --- | --- | --- | --- |
| Lyophilised without heating | — | 100 | 100 |
| 100 | 1 | 104 | 24 |
|  | 2 | 91 | 22 |
|  | 4 | 85 | — |
|  | 8 | 67 | — |
| 105 | ½ | 107 | 19 |
|  | 1 | 103 | — |
|  | 2 | 99 | — |
|  | 4 | 92 | — |
| 110 | ½ | 102 | — |
|  | 1 | 89 | — |
|  | 2 | 89 | — |
|  | 4 | 78 | — |
| 115 | ½ | 101 | — |
|  | 1 | 104 | — |
|  | 2 | 75 | — |
|  | 4 | 66 | — |

The results shown in the table above indicate the heat-protective effect of the albumin and show that it is possible to apply heat for up to approximately a maximum of 4 hours at a temperature of 100-105° C., 2 hours at 110° C. and 1 hour at 115° C. with a recovery of activity of 90±5% or higher.

EXAMPLE 3

In order to evaluate the stability of the lyophilised product the following final products were prepared.

| Preparation | Thrombin activity (UI) | Metered/ regenerated volume (ml) | Albumin (%) | Sodium chloride (M) | Glycine (M) |
| --- | --- | --- | --- | --- | --- |
| 119392 131294 131992 | 10000 | 20 | 0.25 | 0.15 | 0.05 |

These preparations were stored at 5 and 30° C. and samples were analysed at different periods of time, with no signs of instability in the parameters analysed being observed, and obtaining the following activity recoveries (%):

| Prepa-ration | Initial value | 3 months | | 6 months | | 9 months | | 12 months | | 18 months | | 24 months | |
|---|---|---|---|---|---|---|---|---|---|---|---|---|---|
| | | 5° C. | 30° C. | 5° C. | 30° C. | 5° C. | 30 C. | 5° C. | 30° C. | 5° C. | 30° C. | 5° C. | 30° C. |
| 119392 | 100% | 109.4 | 99.8 | 95.6 | 93.9 | 94.1 | 92.6 | 94.6 | 84.5 | 105.7 | 91.8 | 100.1 | 92.4 |
| 131294 | | 87.7 | 86.5 | 86.8 | 83.1 | 79.0 | 80.5 | 94.5 | 84.1 | 97.4 | 85.1 | 104.3 | 84.1 |
| 131992 | | 95.2 | 90.3 | 89.2 | 76.0 | 93.4 | 79.0 | 103.1 | 80.5 | 103.7 | 88.9 | 102.5 | 79.0 |

EXAMPLE 4

The following final products were prepared in order to evaluate the stability of the frozen product.

| Prepa-ration | Thrombin (IU) | Volume (ml) | Albumin (%) | Sodium chloride (M) | Glycine (M) | Calcium chloride (mg) |
|---|---|---|---|---|---|---|
| 219390 232592 302493 | 500 | 1 | 0.25 | 0.15 | 0.05 | 5.88 |
| 219391 232593 302492 | 1500 | 3 | 0.25 | 0.15 | 0.05 | 17.64 |
| 232594 302491 306591 | 2500 | 5 | 0.25 | 0.15 | 0.05 | 29.4 |

These preparations were stored at −18° C. and samples of them were analysed at different periods of time, with no instability in the parameters analysed being observed and obtaining the following recoveries of activity (%):

| | Initial Value | 3 months | 6 months | 9 months | 12 months |
|---|---|---|---|---|---|
| 219390 | 100% | 100.8 | 102.8 | 96.7 | 113.5 |
| 232592 | | 96.1 | 99.5 | 99.5 | nd |
| 302493 | | 99.2 | 93.4 | 91.1 | nd |
| 219391 | | 95.9 | 102.0 | 108.9 | 113.6 |
| 232593 | | 99.1 | 101.3 | 100.4 | nd |
| 302492 | | 100.0 | 92.0 | 89.1 | nd |
| 232594 | | 102.3 | 103.7 | 100.9 | nd |
| 302491 | | 94.1 | 92.2 | 88.3 | nd |
| 306591 | | 92.8 | 91.9 | nd | nd |

(nd: not determined)

Stability in solution at 5 and 25° C. was also investigated for some of these preparations, with no signs of instability in the parameters analysed being observed and obtaining the following recoveries of activity (%):

| | Initial value | 12 hours | | 24 hours | | 48 hours | | 72 hours | |
|---|---|---|---|---|---|---|---|---|---|
| | | 5° C. | 25° C. | 5° C. | 25° C. | 5° C. | 25° C. | 5° C. | 25° C. |
| 232592 | 100% | 105.6 | 99.2 | 107.4 | 103.6 | 97.4 | 97.2 | 107 | 96.8 |
| 302493 | | 99.8 | 97.9 | 91.5 | 88.2 | 88.4 | 88.4 | 92.3 | 84.9 |
| 302491 | | 97.1 | 95.6 | 93.0 | 97.1 | 99.3 | 87.2 | 102 | 94.9 |
| 306591 | | 93.1 | 89.3 | 93.8 | 89.3 | 95.3 | 93.6 | 93.6 | 88.9 |

Although the invention has been described in its essential features on the basis of illustrative examples, it should be understood that the description is not designed to restrict the scope of this invention, which is defined by the following claims.

The invention claimed is:

1. A process for the preparation of a thrombin composition, consisting essentially of the following steps in the sequence set forth:
   a. obtaining a purified thrombin solution with a specific activity of 1500 IU of thrombin/mg of protein or more and a strength of 500 IU thrombin/ml or more;
   b. stabilizing and adjusting the final formulation of the thrombin solution through adding and mixing with human albumin at a concentration of greater than 0.05% (w/v) and less than or equal to 1% (w/v) and a neutral salt; and
   c. applying a double nanofiltration system to the thrombin solution, wherein the double nanofiltration is performed in series, with a filtrate from a first nanofiltration feeding into a second nanofiltration, and each nanofiltration in the double nanofiltration system has a pore size of 15 nm, wherein the thrombin solution obtained from the second nanofiltration is filled into a container without any subsequent treatment for adjustment of the formula or final composition.

2. The process of claim 1, wherein the nanofiltration is applied to between 5 and 30 liters of solution per square meter of filtration area for each nanofilter.

3. The process of claim 1, wherein the solution filled into the container is subjected to a freezing process.

4. The process of claim 1, wherein the solution filled into the container is subjected to a lyophilization, wherein a lyophilized composition is obtained.

5. The process of claim 4, wherein the the lyophilized composition is dry heated for a time of between half an hour and eight (8) hours at a temperature of between 90 and 115° C.

6. The process of claim 5, wherein the the lyophilized composition is dry heated for a time of between 1 to 2 hours at a temperature of 100° C.

7. The process of claim 1, wherein the neutral salt is sodium chloride used at a concentration of at least 0.05 molar.

8. The process of claim 1, wherein the container is a vial, bottle or syringe.

* * * * *